(12) United States Patent
Doose et al.

(10) Patent No.: US 10,610,261 B2
(45) Date of Patent: Apr. 7, 2020

(54) POST-OPERATIVELY ADJUSTABLE ANGLED ROD

(71) Applicant: NUVASIVE, INC., San Diego, CA (US)

(72) Inventors: Justin Doose, San Diego, CA (US); Mark Ojeda, San Diego, CA (US); Matthew Tobias Jacobs, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 15/432,656

(22) Filed: Feb. 14, 2017

(65) Prior Publication Data

US 2017/0231664 A1    Aug. 17, 2017

Related U.S. Application Data

(63) Continuation of application No. PCT/US2017/017697, filed on Feb. 13, 2017.

(60) Provisional application No. 62/294,988, filed on Feb. 12, 2016.

(51) Int. Cl.
*A61B 17/70*        (2006.01)

(52) U.S. Cl.
CPC ...... *A61B 17/7016* (2013.01); *A61B 17/7023* (2013.01); *A61B 17/7055* (2013.01)

(58) Field of Classification Search
CPC ............ A61B 17/7016; A61B 17/7023; A61B 17/7055; A61B 17/7032; A61B 17/7011; A61B 17/7049; A61B 17/8891; A61B 17/8085; A61B 17/7059; A61B 17/8052; A61B 17/8605; A61B 17/8886; A61B 17/8071; A61B 17/7253; A61B 17/8863; A61B 17/00004; A61F 2/2846; A61F 2/30771; Y10S 606/902; Y10S 606/903
USPC ......... 606/246–279; 623/17.11–17.16, 17.19
See application file for complete search history.

(56) References Cited

U.S. PATENT DOCUMENTS

| | | |
|---|---|---|
| 1,365,532 A | 1/1921 | Mountain |
| 2,077,844 A | 4/1937 | Leighton |
| 3,342,922 A | 9/1967 | Karpovich |
| 3,385,615 A | 5/1968 | Hussey |

(Continued)

OTHER PUBLICATIONS

International Search Report dated Aug. 17, 2017 for International Application No. PCT/US2017/017697, 8 pages.

(Continued)

*Primary Examiner* — Pedro Philogene

(57) ABSTRACT

A jointed rod assembly for use in a spinal fixation construct involves a caudal rod portion connectable to an adjustment mechanism, and a cranial rod portion connectable to the adjustment mechanism. The adjustment mechanism is configured to rotate the caudal and cranial rod portions relative to one another about a joint axis that is generally perpendicular to the longitudinal axes of the caudal and cranial rod portions. The caudal and cranial rod portions may be dimensioned to be compatible with other pieces of hardware commonly used for spinal fixation, such as bone anchors (e.g., pedicle screws), occipital plates, reducers, and others. The caudal and cranial rod portions are composed of a strong, rigid, non-absorbable, biocompatible material. The jointed rod assembly may be advantageously used in spinal fixation systems and methods of spinal fixation.

19 Claims, 7 Drawing Sheets

(56) References Cited

U.S. PATENT DOCUMENTS

| | | |
|---|---|---|
| 3,816,854 A | 6/1974 | Schlein |
| 4,433,677 A | 2/1984 | Ulrich |
| 5,405,347 A | 4/1995 | Lee et al. |
| 5,509,328 A | 4/1996 | Lai |
| 5,643,263 A | 7/1997 | Simonson |
| 5,645,544 A | 7/1997 | Tai |
| 5,662,653 A | 9/1997 | Songer |
| 5,885,285 A | 3/1999 | Simonson |
| 5,947,967 A | 9/1999 | Barker |
| 5,984,923 A | 11/1999 | Breard |
| 6,007,536 A | 12/1999 | Yue |
| 6,183,473 B1 | 2/2001 | Ashman |
| 6,238,396 B1 | 5/2001 | Lombardo |
| 6,284,014 B1 | 9/2001 | Carden |
| 6,296,644 B1 | 10/2001 | Saurat |
| 6,402,749 B1 | 6/2002 | Ashman |
| 6,471,703 B1 | 10/2002 | Ashman |
| 6,551,318 B1 | 4/2003 | Stahurski |
| 6,562,038 B1 | 5/2003 | Morrison |
| 6,579,292 B2 | 6/2003 | Taylor |
| 6,620,164 B2 | 9/2003 | Ueyama |
| 6,626,906 B1 | 9/2003 | Young |
| 6,648,887 B2 | 11/2003 | Ashman |
| 6,652,527 B2 | 11/2003 | Zucherman |
| 6,663,632 B1 | 12/2003 | Frigg |
| 6,685,705 B1 | 2/2004 | Taylor |
| 6,689,133 B2 | 2/2004 | Morrison |
| 6,832,999 B2 | 12/2004 | Ueyama et al. |
| 6,872,209 B2 | 3/2005 | Morrison |
| 7,517,359 B2 | 4/2009 | Drewry et al. |
| 8,057,472 B2 | 11/2011 | Walker |
| 8,197,490 B2 | 6/2012 | Pool |
| 8,382,756 B2 | 2/2013 | Pool |
| 8,419,734 B2 | 4/2013 | Walker |
| 8,449,543 B2 | 5/2013 | Pool |
| 8,715,159 B2 | 5/2014 | Pool |
| 8,734,488 B2 | 5/2014 | Pool |
| 8,852,187 B2 | 10/2014 | Pool |
| 8,974,463 B2 | 3/2015 | Pool |
| 9,179,938 B2 | 11/2015 | Pool |
| 9,179,960 B2 | 11/2015 | Walker |
| 9,186,183 B2 | 11/2015 | Pool |
| 9,757,159 B2 | 9/2017 | Pool |
| 9,770,274 B2 | 9/2017 | Pool |
| 9,848,914 B2 | 12/2017 | Pool |
| 2002/0138077 A1 | 9/2002 | Ferree |
| 2002/0193794 A1 | 12/2002 | Taylor |
| 2003/0171751 A1 | 9/2003 | Ritland |
| 2003/0176863 A1 | 9/2003 | Ueyama |
| 2003/0176864 A1 | 9/2003 | Ueyama |
| 2003/0191473 A1 | 10/2003 | Taylor |
| 2004/0002708 A1 | 1/2004 | Ritland |
| 2004/0015166 A1 | 1/2004 | Gorek |
| 2004/0039384 A1 | 2/2004 | Boehm |
| 2004/0133203 A1 | 7/2004 | Young et al. |
| 2005/0113835 A1 | 5/2005 | Ashman |
| 2005/0228376 A1 | 10/2005 | Boomer et al. |
| 2010/0217271 A1* | 8/2010 | Pool .............. A61B 17/7004 606/90 |
| 2011/0087288 A1* | 4/2011 | Stevenson ........ A61B 17/7037 606/250 |
| 2012/0078306 A1* | 3/2012 | Lynch ............. A61B 17/705 606/264 |
| 2014/0088649 A1 | 3/2014 | Refai |
| 2014/0214083 A1* | 7/2014 | Refai ............. A61B 17/7019 606/256 |
| 2014/0228891 A1* | 8/2014 | Hammer ......... A61B 17/7055 606/278 |
| 2015/0105826 A1* | 4/2015 | Green ............ A61B 17/707 606/263 |

OTHER PUBLICATIONS

Written Opinion of the International Searching Authority dated Aug. 17, 2017 for International Application No. PCT/US2017/017697, 11 pages.

* cited by examiner

POST-OPERATIVELY ADJUSTABLE ANGLED ROD

CROSS-REFERENCE TO RELATED APPLICATIONS

This application is a continuation of International Pat. App. No. PCT/US17/17697, filed 13 Feb. 2017 (pending). International Pat. App. No. PCT/US17/17697 cites the priority of U.S. patent application Ser. No. 62/294,988, filed on 12 Feb. 2016. Both of the foregoing related applications are incorporated herein by reference in their entireties.

BACKGROUND

Field

The present disclosure relates generally to medical devices, and specifically to surgical instruments and methods for performing spinal procedures.

Background

The spine is critical in human physiology for mobility, support, and balance. The spine protects the nerves of the spinal cord, which convey commands from the brain to the rest of the body, and convey sensory information from the nerves below the neck to the brain. Even minor spinal injuries can be debilitating to the patient, and major spinal injuries can be catastrophic. The loss of the ability to bear weight or permit flexibility can immobilize the patient. Even in less severe cases, small irregularities in the spine can put pressure on the nerves connected to the spinal cord, causing devastating pain and loss of coordination.

The spinal column is a bio-mechanical structure composed primarily of ligaments, muscles, bones, and connective tissue that forms a series of vertebral bodies stacked one atop the other and intervertebral discs between each vertebral body. The spinal column provides support to the body and provides for the transfer of the weight and the bending movements of the head, trunk and arms to the pelvis and legs; complex physiological motion between these parts; and protection of the spinal cord and the nerve roots.

The stabilization of the vertebra and the treatment for above described conditions is often aided by a surgically implanted fixation device which holds the vertebral bodies in proper alignment and reduces the patient's pain and prevents neurologic loss of function. Spinal fixation is a well-known and frequently used medical procedure. Spinal fixation systems are often surgically implanted into a patient to aid in the stabilization of a damaged spine or to aid in the correction of other spinal deformities. Existing systems often use a combination of rods, plates, pedicle screws, bone hooks, locking screw assemblies and connectors for fixing the system to the affected vertebrae. The system components may be rigidly locked together to fix the connected vertebrae relative to each other, stabilizing the spine until the bones can fuse together.

Posterior fusion and accompanying fixation may be the preferred approach for patients in whom the construct requires an extension from the cervical spine to the occipital bone (e.g. where there is instability at the craniocervical junction). In this scenario, the cranial end of the rod is attached to the occipital bone (the back of the skull), via an occipital keel plate or other suitable connector. A large bend in the rod is generally required to accommodate the transition from the plane of the spine to the skull, which can make the process of aligning the rod and connector for coupling difficult. This difficulty is further exacerbated because it is not only necessary to make the rod and occipital connector meet, but to do so at a position that properly orients the skull relative to the spine.

Fusing the cranial cervical junction bars movement of the head relative to the spine, thus it is desirable to position the skull such that the patient will have a comfortable, horizontal gaze (such that the patient is not naturally looking too high or too low while in a neutral standing position). While certain devices, such as adjustable occipital plate connectors, and adjustable angle rods have been developed to facilitate alignment of the rod and the occipital plate (or other connector), these require that the surgeon estimate the orientation of the head relative to the spine during the surgery while the patient is both in the prone position and unable to provide feedback to the surgeon. If the surgeon miscalculates during surgery, the patient could have a resulting orientation of the skull in which the patient's gaze is offset. The offset gaze will force the patient to constantly roll the eyes in awkward ways to have a normal frontal field of vision; and will result in the patient's total field of vision being offset. Consequently there is a need in the art for a way to adjust or set the orientation of the cranial cervical junction post-operatively if necessary.

SUMMARY

The present disclosure describes a jointed spinal rod, including parts thereof, useful for fixing the relative positions of spinal vertebrae, while allowing the angle of fixation to be adjusted non-invasively postop. This is accomplished through use of a magnetic control mechanism of the angle of fixation. Using an external spinning magnetic field, the control mechanism is induced to rotate, which actuates a change in angle. Systems and methods employing the jointed spinal rod are also provided. The posterior cervical fixation system facilitates securing of an orthopedic rod to the spine and occipital bone, while permitting postoperative adjustment of the skull angle relative to the spine before fusion occurs.

In a first aspect, a jointed spinal rod assembly is provided, comprising: a caudal rod portion connectable to an adjustment mechanism; and a cranial rod portion connectable to the adjustment mechanism; wherein the adjustment mechanism is configured to rotate the caudal and cranial rod portions relative to one another about a joint axis that is generally perpendicular to the longitudinal axes of the caudal and cranial rod portions when exposed to a rotating magnetic field.

In a second aspect, a cervical fixation system for fixing the relative positions of a cervical vertebra and an occipital bone in a subject is provided, the system comprising: a jointed spinal rod assembly having a caudal rod portion connectable to an adjustment mechanism, and a cranial rod portion connectable to the adjustment mechanism, said spinal rod assembly having a longitudinal length sufficient to extend from the vertebra to the occipital bone, and wherein the adjustment mechanism is configured to rotate the caudal and cranial rod portions relative to one another about a joint axis that is generally perpendicular to the longitudinal axes of the caudal and cranial rod portions in response to a rotating magnetic field; a bone anchor having a bone fastener connected to a rod housing, said rod housing dimensioned to accept the caudal rod portion of the spinal rod assembly; and an occipital plate member having a fixation screw, and a rod receiver dimensioned to accept the cranial rod portion of the spinal rod assembly.

In a third aspect, a method of fixing the relative positions of a cervical vertebra and an occipital bone in a subject is provided, the method comprising: fastening a bone anchor to the cervical vertebra of the subject; fastening an occipital plate member to the occipital bone of the subject; connecting a jointed spinal rod assembly comprising a caudal rod portion and a cranial rod portion to the bone anchor via the caudal rod portion and to the occipital plate via the cranial rod portion, wherein the caudal rod portion is connectable to an adjustment mechanism, and the cranial rod portion is connectable to the adjustment mechanism, wherein the adjustment mechanism is configured to rotate the caudal and cranial rod portions relative to one another about a joint axis that is generally perpendicular to the longitudinal axes of the caudal and cranial rod portions when exposed to a rotating magnetic field; and adjusting the relative inclination of the caudal rod portion of the spinal rod assembly to the cranial rod portion of the rod assembly by exposing the first magnet to a rotating magnetic field of sufficient strength to cause rotation of the first magnet, thereby causing the caudal rod portion to rotate relative to the cranial rod portion.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

DETAILED DESCRIPTION

Illustrative embodiments of a jointed spinal rod, systems, and methods for use thereof, are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The jointed spinal rod, systems, and methods for use thereof disclosed herein boasts a variety of inventive features and components that warrant patent protection, both individually and in combination.

Figure 2:
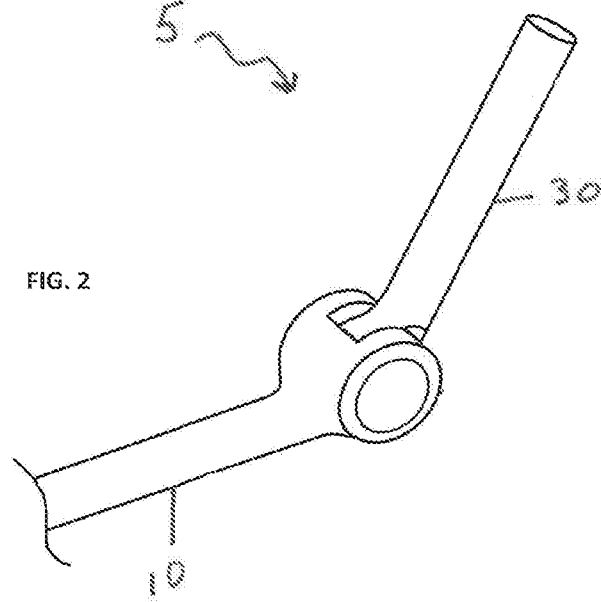
FIG. 2. A perspective view of an exemplary embodiment of the jointed spinal rod assembly.

A jointed spinal rod assembly 5 is provided, capable of being adjusted in angularity postoperatively without further surgeries. As shown in the illustrative embodiment in FIG. 2, a general embodiment of the jointed rod assembly 5 comprises a caudal rod portion 10 connected to an adjustment mechanism 20, and a cranial rod portion 30 connected to the adjustment mechanism 20. The adjustment mechanism 20 is configured to rotate the caudal 10 and cranial 30 rod portions relative to one another about a joint axis that is generally perpendicular to the longitudinal axes of the caudal and cranial rod portions. The caudal 10 and cranial 30 rod portions may be dimensioned to be compatible with other pieces of hardware commonly used for spinal fixation, such as bone anchors (e.g., pedicle screws), occipital plates, reducers, and others. The caudal 10 and cranial 30 rod portions are composed of a strong, rigid, non-absorbable, biocompatible material. Specific examples of such suitable materials include titanium, alloys of titanium, steel, and stainless steel. Parts of the jointed spinal rod 5 could conceivably be made from non-metallic biocompatible materials, which include aluminum oxide, calcium oxide, calcium phosphate, hydroxyapatite, zirconium oxide, and polymers such as polypropylene.

The cranial 30 and caudal 10 rod portions will generally be dimensioned to reach a cervical vertebra in a subject (on the caudal side) and reach the occipital bone of the subject (on the cranial side). These lengths will of course vary depending on the size of the subject, and may be customized for a given subject. In some embodiments, such lengths could be sufficient to extend from the occipital bone 50 to a cervical vertebra of a pediatric patient. In other such embodiments the lengths could be sufficient to extend from the occipital bone 50 to a cervical vertebra of an adult patient.

Figure 3:
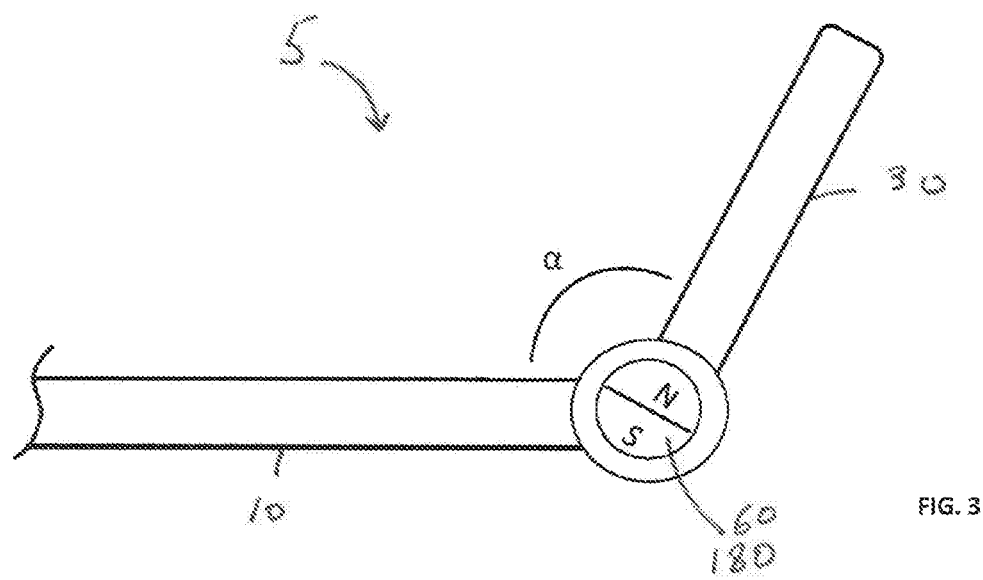
FIG. 3. A side view of an exemplary embodiment of the jointed spinal rod assembly comprising a dipole magnet.

Some embodiments of the adjustment mechanism 20 are configured to rotate when exposed to a rotating magnetic field; this can be accomplished by various means. Some embodiments of the adjustment mechanism 20 are operatively linked to a first rotatable magnet 60 configured to rotate when exposed to a rotating magnetic field, such that the adjustment mechanism 20 is configured to rotate the caudal rod portion 10 about the joint axis relative to the cranial rod portion 30 in response to the rotation of the rotatable magnet 60. The magnet 60 is composed of a magnetic material, such as a ferromagnetic material. For example, the rotatable magnet 60 may have at least one circular cross-section 100 to enable it to rotate smoothly inside of a housing 80 (e.g., a sphere, cylinder, disc, cone, ellipsoid, etc.) The rotatable magnet 60 may in some cases be mounted within the jointed rod 5. In the example shown in FIG. 3, the first magnet 60 is a disc-shaped dipole magnet, mounted within the joint 160 with an axis of rotation perpendicular to longitudinal axes of both the caudal and cranial rods. In an alternative embodiment shown in FIG. 4, the first magnet 60 is a disc-shaped quadrupole magnet, also mounted within the joint 160 with an axis of rotation perpendicular to longitudinal axes of both the caudal and cranial rods (10 and 30, respectively). In further embodiments the first magnet 60 is any multipolar magnet.

As a safety precaution, a magnetic immobilization plate 120 may be positioned, sufficiently close to the rotatable magnet 60 to cause the rotatable magnet 60 to adhere to the immobilization plate 120 in the absence of a strong external magnetic field. The magnetic immobilization plate 120 will hold the rotating magnet 60 in position, preventing it from rotating, until a stronger magnetic field is applied, such as the rotating magnetic field that is used to adjust the relative orientations of the cranial and caudal rods (30 and 10, respectively). Like the rotating magnet 60, the immobilization plate 120 may be constructed from a suitable magnetic material, such as a ferromagnetic material.

Some embodiments of the adjustment mechanism 20 allow relative rotation of the caudal and cranial rod portions (10, 30) about exactly one axis, like a hinge. Further embodiments may allow relative rotation of the two portions about more than one axis. Embodiments that allow relative rotation about exactly one axis have the advantage of stability, whereas embodiments that allow relative rotation about more than one axis have the advantage of flexibility. Accordingly, rotation may be achieved using a single actuator or multiple actuators.

Figure 10:
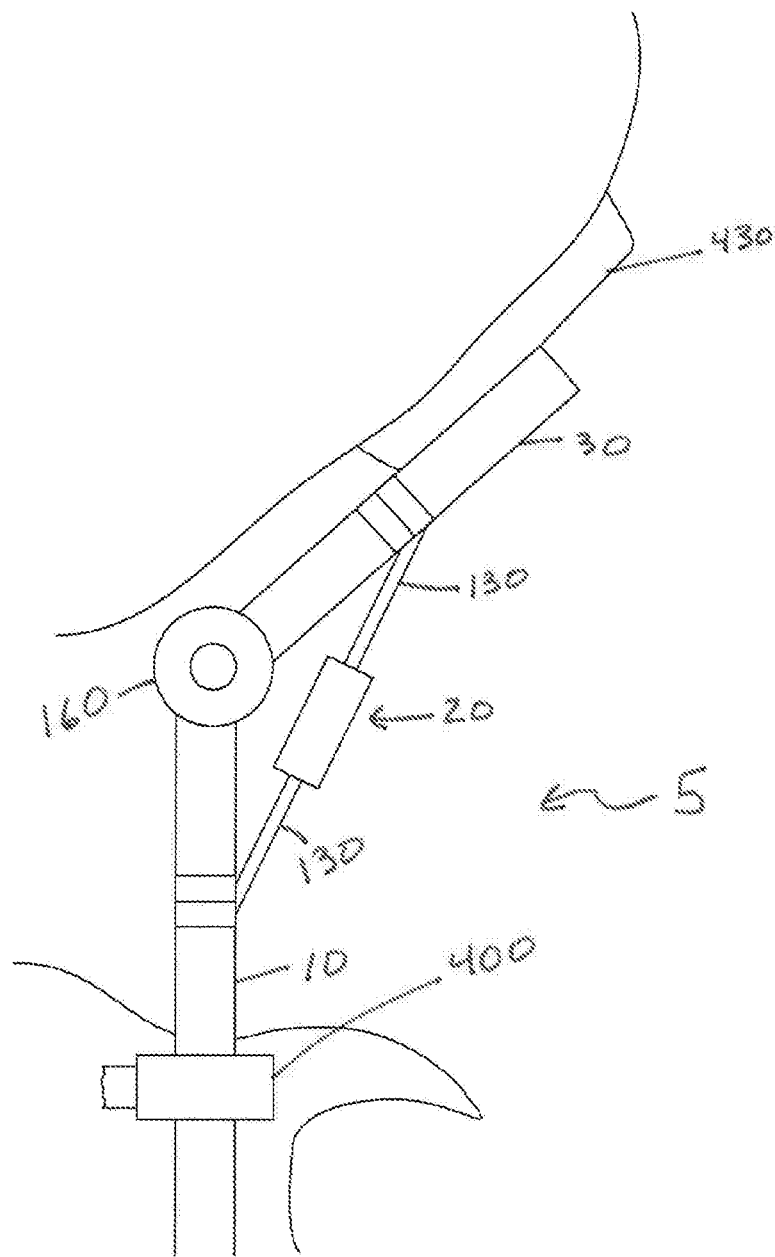
FIG. 10. Detail of an alternative embodiment of the jointed spinal rod assembly.

In an alternative embodiment of the adjustment mechanism 20 shown in FIG. 10, the adjustment mechanism 20 connects to the caudal and cranial rods (10, 30) above the joint 160 by a pair of linkage arms 130. The combined length of the two linkage arms 130 is adjusted in response to a rotating magnetic field, such that elongation of their combined length causes the 20 relative angle between the cranial 30 and caudal 10 portions to increase, and such that shortening of their combined length causes the relative angle between the cranial 30 and caudal 10 portions to decrease. Adjustment of the linkage arms 130 may be achieved using a rotatable magnet 60, configured to change the combined lengths of the linkage arms 130 when it rotates. For example, the rotatable magnet 60 could drive a threaded shaft at the end of 25 one or both linkage arms 130, and the housing 80 of the adjustment mechanism 20 could include a threaded orifice engaged to the threaded shaft.

In embodiments of the adjustment mechanism 20 comprising the first magnet 60, there are distinct advantages to constructing the adjustment mechanism 20 from a nonabsorbable biocompatible material that is not magnetic or weakly magnetic. Namely, the non-magnetic or weakly magnetic material will not interfere with the motion of the first magnet 60 when exposed to an external rotating magnetic field. Specific examples of such nonmagnetic nonabsorbable biocompatible material include titanium, alloys of titanium, aluminum oxide, calcium oxide, calcium phosphate, hydroxyapatite, zirconium oxide, and polymers such as polypropylene. Examples of weakly magnetic materials include paramagnetic materials and diamagnetic materials. In a specific embodiment, the weakly magnetic material is austenitic stainless steel.

Figure 4:
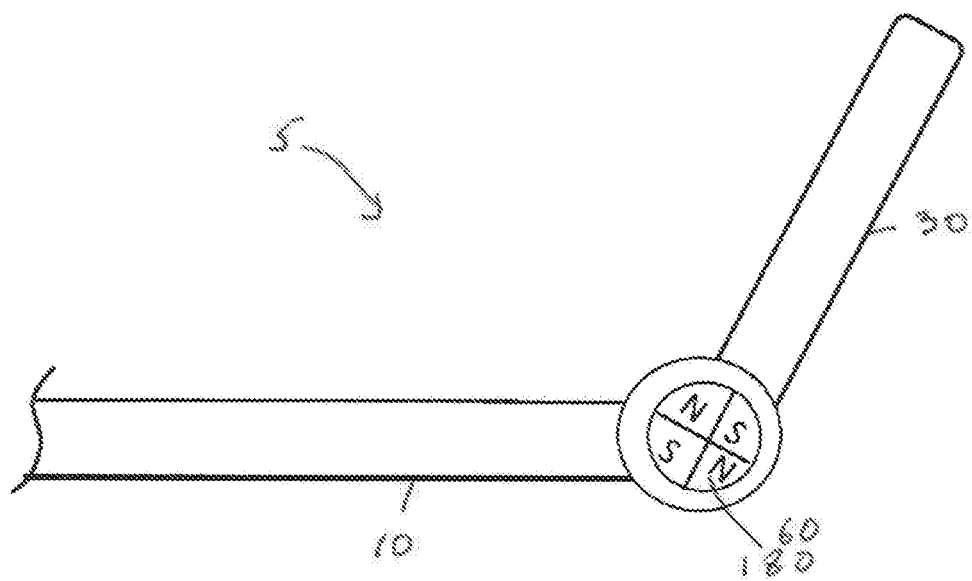
FIG. 4. A side view of an exemplary embodiment of the jointed spinal rod assembly comprising a quadrupole magnet.
Figure 5:
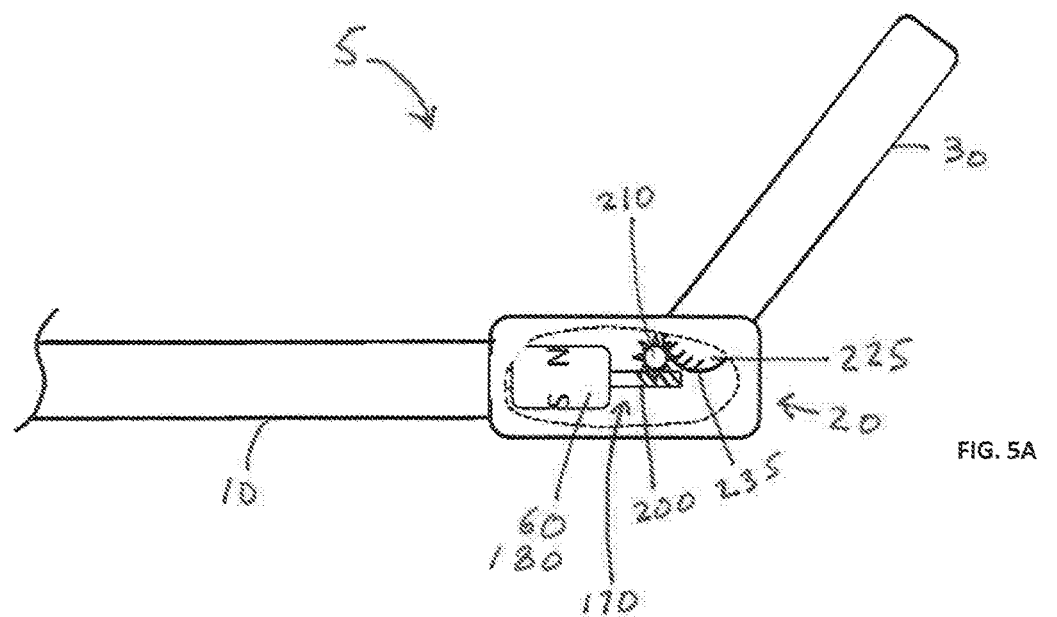
FIG. 5A. A side view of an exemplary embodiment of the jointed spinal rod assembly, showing a cutaway of the adjustment mechanism.
FIG. 5B. A close-up cutaway view of an alternative embodiment of the adjustment mechanism.

Note that in the embodiments shown in FIGS. 4 and 5 the first magnet 60 directly drives the joint. However, the first magnet 60 may also drive the joint 160 indirectly. For example, the first magnet 60 may drive the joint 160 by means of a gear train 170. The use of a gear train 170 has the advantage of allowing an unequal ratio between the angular motion of the magnet 60 and the angular motion of the joint 160. For example, if the gear ratio is less than 1:1 (joint 160:magnet 60), then delicate changes in the angulation of the jointed rod 5 may be accomplished, and increased torque may be realized with less force. On the other hand, if the gear ratio is greater than 1:1, the angulation of the jointed rod 5 may be accomplished at greater speeds with less torque.

A specific example of an adjustment mechanism 20 with a gear train 170 is shown in FIG. 5A. The illustrated embodiment comprises a cylindrical magnet 180 mounted to rotate about an axis that is parallel to the longitudinal axis of the caudal rod portion 10. The cylindrical magnet 180 spins a coaxial threaded rod 200 (such as a screw or a worm) that is engaged to a toothed wheel 210 (such as a gear or worm wheel), the toothed wheel 210 having an axis perpendicular to the axes of the magnet 180 and the threaded rod 200. In this configuration rotation of the magnet 180 drives rotation of the threaded rod 200, which in turn drives rotation of the toothed wheel 210 at a perpendicular axis. The cranial rod portion 30 is connected to the joint 160 by a fulcrum or an axle 230 (such as a pin) near its caudal end 225. The caudal end 225 of the cranial rod portion 30 has a series of grooves 235 that mate with the teeth 245 on the toothed wheel 210, such that the rotation of the toothed wheel 210 causes the cranial rod portion 30 to rotate about the fulcrum or axle 230, thus changing the relative angle between the caudal and cranial rod portions (10, 30).

Figure 9:
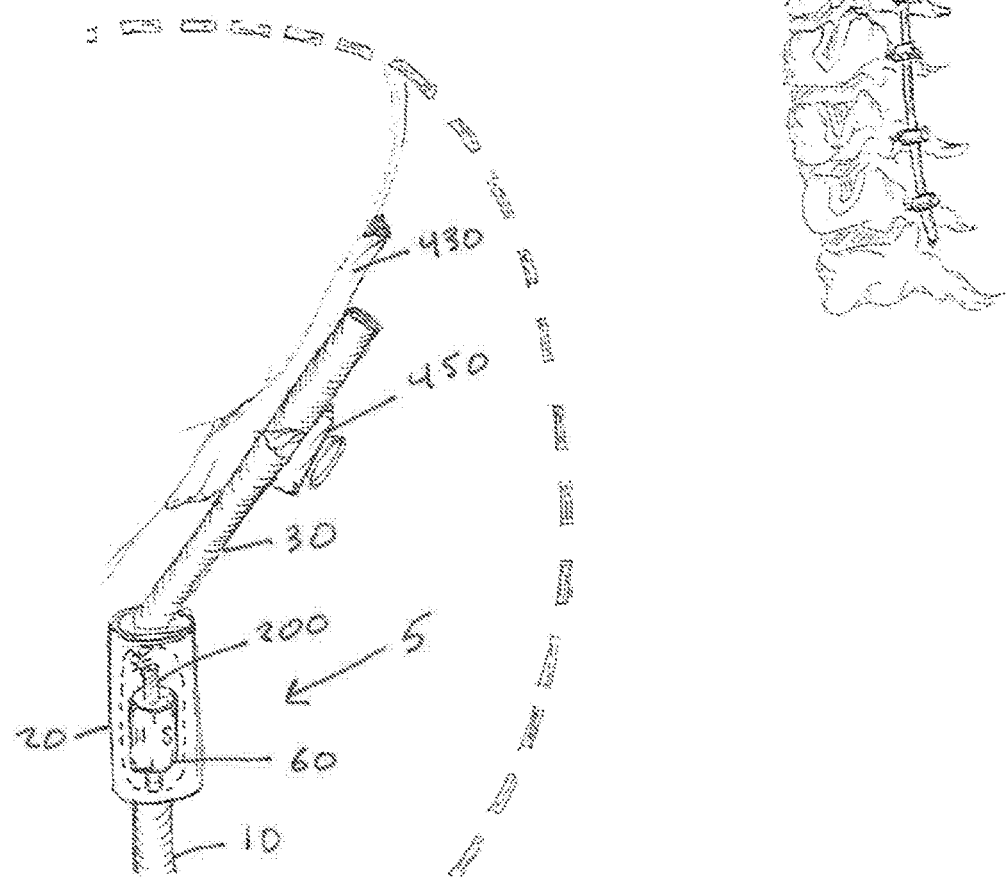
FIG. 9. Detail of the embodiment of the jointed spinal rod assembly in the system shown in FIG. 8.

Additional examples of an adjustment mechanism 20 with a gear train 170 are shown in FIGS. 5B and 9. The illustrated embodiments comprise a cylindrical magnet 180 mounted to rotate about an axis that is parallel to the longitudinal axis of the caudal rod portion 10. The cylindrical magnet 180 spins a coaxial threaded rod 200 (such as a screw or a worm). The cranial rod portion 30 is connected to the joint 160 by a fulcrum or an axle 230 (such as a pin) near its caudal end 225. Unlike the embodiment illustrated in FIG. 5A, in FIGS. 5B and 9 the threaded rod 200 is directly engaged to the cranial rod portion 30. To facilitate this, the caudal end 225 of the cranial rod portion 30 has a plurality of thread engagement features 240, such as teeth or grooves, engaged to the threaded rod 200. As a result, rotation of the threaded rod 200 causes the cranial rod portion 30 to rotate about the fulcrum or axle 230.

The adjustment mechanism 20 may comprise a locking mechanism to prevent any change in relative inclination between the caudal and cranial rod portions (10, 30) when the locking mechanism is engaged, but allow such changes when not engaged. The locking mechanism may be disengaged prior to adjustment and reengaged after adjustment. The locking mechanism may also be controlled by an external drive device. A specific embodiment of the locking mechanism comprises a magnetically driven set screw. The magnetically driven set screw may be oriented such that the external drive controller can be positioned to drive only one of the set screw and first magnet 60, and then repositioned to drive the other. For example, the set screw and the first magnet 60 may be oriented such that each is driven by magnetic fields with perpendicular orientations (such that the field driving the first magnet 60 will not rotate that set screw, and vice-versa). According to one embodiment, the locking mechanism may be a set screw situated in the hinge joint 160 opposite the first magnet 60. Complementary surfaces of the caudal rod portion 10 and the cranial rod portion 30 may have ridged surfaces that interdigitate, thus resisting rotation, when pressed into contact with each other by the advancing set screw. Alternatively, a locking pin or shaft could be advanced with the set screw into the hinge joint 160 to inhibit movement of the joint. Such a locking pin or shaft could be driven directly by a locking magnet or driven by a locking magnet via a gear train 170. Ratchet configurations that resist movement in one direction are also contemplated. In embodiments controlled by an external drive device, the locking mechanism is capable of being engaged post-operatively. Further such embodiments may be capable of being disengaged post-operatively.

In bilateral embodiments of the system, the locking mechanism may be positioned between two jointed spinal rods (305, 310) with two corresponding adjustment mechanisms 20, to lock (and optionally unlock) both simultaneously. An exemplary such embodiment includes a cylindrical lock magnet with a longitudinal axis approximately perpendicular to the longitudinal axis of the caudal 10 and cranial 30 rods. The cylindrical lock magnet spins on its longitudinal axis when exposed to a rotating magnetic field, driving a set screw either directly or through a gear train 170.

The magnetically driven set screw (or other magnetically driven locking mechanism) may itself be held in place by a second magnetic immobilization plate. Like the first magnetic immobilization plate 120 described above, the second magnetic immobilization plate will hold the set screw in place by adhering magnetically to the set screw in the absence of a stronger magnetic field. However, in the presence of a strong magnetic field (such as the rotating magnetic field that drives the set screw), the set screw will not adhere to the second immobilization plate, and will be free to rotate.

Figure 6:
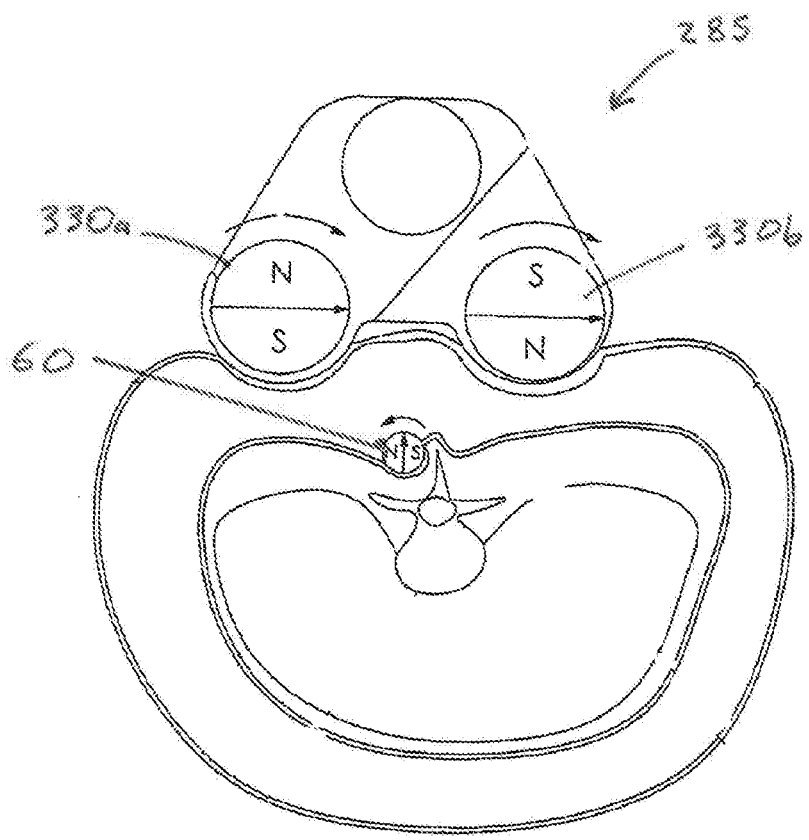
FIG. 6. A caudal cross-sectional view of a subject with an exemplary embodiment of the cervical fixation system implanted in the subject, showing an embodiment of the controller positioned to cause rotation of the magnet in the jointed spinal rod.

The first magnet 60 may be driven by a rotating magnetic field that originates external to the subject. This may be accomplished using an external rotating magnet 330 or array of magnets, or using an electrically induced magnetic field. One embodiment of the external adjustment device 285, illustrated in FIG. 6, is configured for placement on or adjacent to the skin of the subject and includes at least one magnet 330 ("external magnet") configured for rotation. The illustrated embodiment also has a motor 340 configured to rotate the external magnet 330, whereby rotation of the external magnet 330 effectuates rotational movement of the first magnet 60 of the adjustable rod and alters the angle (α). Other means of rotating the external magnet 330 may of course be used. As shown in FIG. 6, the external adjustment device 285 may have two external magnets (330a, 330b). The two external magnets (330a, 330b) may be configured to rotate at any suitable rate, and in a specific embodiment they are configured to rotate at the same rate. In further embodiments the external magnets (330a, 330b) are configured to rotate at the same rate such that the positive and negative poles of each external magnet (330a, 330b) are aligned. Stated another way, in such embodiments the positive ("North") pole of the first external magnet 330a will be at 0° when the positive pole of the second external magnet 330b is at 180°, and the negative ("South") pole of the first external magnet 330a will be at 180° when the negative pole of the second external magnet 330b is at 0° (such a configuration is shown in FIG. 6). Because both external magnets (330a, 330b) rotate in the same direction along parallel axes at the same rate this relative configuration will be preserved through multiple cycles.

The jointed spinal rod 5 may be used in a spinal fixation system 370. The spinal fixation system 370 may be a cervical fixation system 380, for fixing the relative positions of a cervical vertebra and an occipital bone in a subject. In a general embodiment of such a system 370, the system 370 comprises any embodiment of the jointed spinal rod assembly 5 described above, in which the spinal rod assembly 5 has a longitudinal length sufficient to extend from the vertebra to the occipital bone; a bone anchor 400 having a bone fastener 410 connected to a rod housing 80, said housing 80 dimensioned to accept the caudal rod portion 10 of the spinal rod assembly 5; and an occipital plate member 430 having a fixation screw 440, and a rod receiver 450 dimensioned to accept the cranial rod portion 30 of the spinal rod assembly 5. The components of the system 370 may be made of any non-absorbable biocompatible material, including those disclosed above as suitable for the jointed rod 5. Exemplary embodiments of the system 370 are illustrated in FIGS. 1 and 8 (with detail of the adjustment mechanism 20 and the occipital 430 plate provided in FIG. 9).

Figure 1:
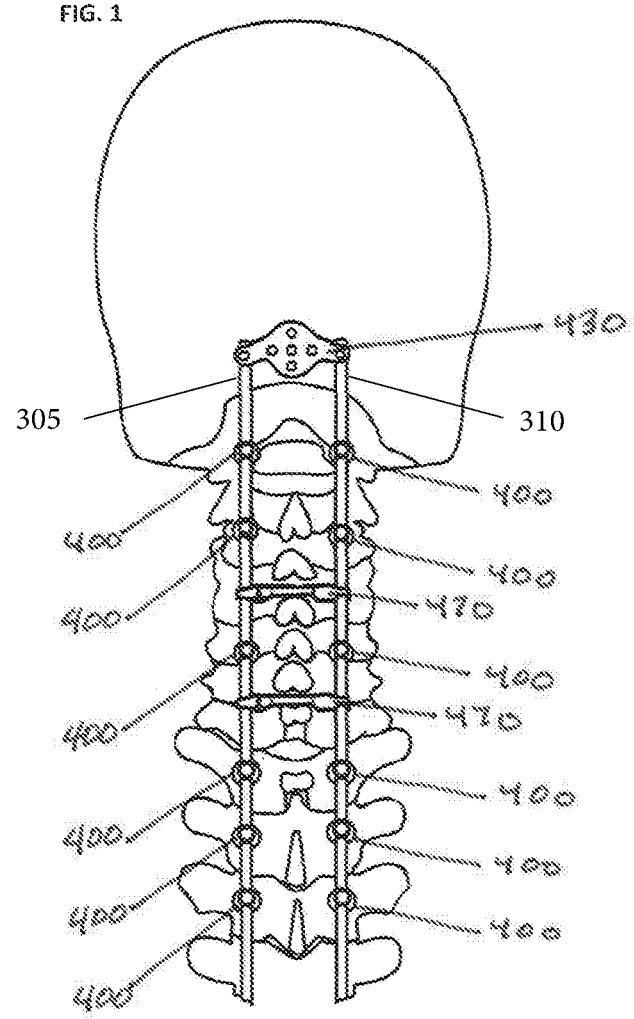
FIG. 1. A posterior view of an exemplary embodiment of the cervical fixation system, showing only the skeletal system of the subject.
Figure 8:
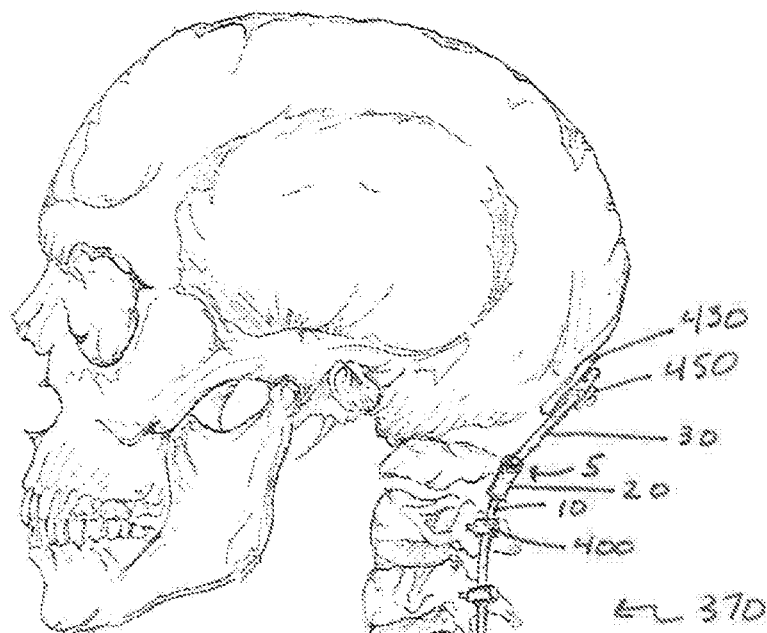
FIG. 8. A side view of a subject with an exemplary embodiment of the cervical fixation system implanted in the subject, showing only the skeletal system of the subject.

FIGS. 1 and 8 illustrate an embodiment of a posterior cervical fixation system installed in across the occipital-cervical junction. As can be seen in FIG. 1, the cervical fixation system 380 may be bilateral, comprising two generally parallel rods (305, 310) running on the posterior surface of the spine. The illustrated embodiment of the system comprises a pair of elongated spinal rods (305, 310), an occipital plate 430, three cross connectors 470, and a plurality of vertebral anchors 480 (pedicle screws in the illustrated embodiments). The posterior cervical fixation system 380 described herein is for attachment to the posterior part of the human spine from the occipital bone to the cervical and/or thoracic vertebrae. Various configurations may be employed in bilateral embodiments. For example, the system may include two jointed rods on either side of the spinous processes, which share a common adjustment mechanism. In a specific such embodiment, the adjustment mechanism is positioned between the two jointed spinal rods, and contains the first magnetic positioned to rotate about an axis that is approximately parallel to the rotation axes of the two joints. As another example, the system may include two rigid spinal rods that connect to a single jointed spinal rod at the cephalad end, and the single jointed spinal rod connects both sides of the bilateral construct to the skull.

As shown in the exemplary embodiments in FIGS. 1 and 9, the occipital plate member 430 will be attached to the occipital bone. Such attachment may be achieved by various means, including via a fixation screw 440. Multiple fixation screws 440 may be used to attach the occipital plate member 430 more securely. The occipital plate member 430 includes a rod receiver 450 dimensioned to accept the cranial rod portion 30 of the spinal rod assembly 5. Bilateral embodiments of the fixation system may comprise a pair of rod receivers (450a, 450b) dimensioned to receive first 305 and second 310 adjustable spinal rods, respectively. The rod receiver 450 or receivers (450a, 450b) may comprise one or more clamping elements 490 to secure the rod to the plate 430. The bone anchor 400 comprises a rod housing 80 configured to accept the caudal rod portion 10, where they may be seated and fastened.

In the illustrated embodiment a plurality of cross-connectors 470 are fastened to the first 305 and second 310 rods, providing lateral stability to the system. The cross-connector 470 may be dimensioned to fit between two spinous processes of the subject, as shown in FIG. 1.

A method of fixing the relative positions of a cervical vertebra and an occipital bone in a subject is provided using the jointed rod disclosed above. Any embodiment of the rod described above that incorporates the first magnet may be employed in the method. In a general embodiment, the method comprises fastening a bone anchor to the cervical vertebra of the subject; fastening an occipital plate member to the occipital bone of the subject; connecting the jointed spinal rod assembly to the bone anchor via the caudal rod portion and to the occipital plate via the cranial rod portion; and adjusting the relative inclination of the caudal rod portion of the spinal rod assembly to the cranial rod portion of the rod assembly by exposing the first magnet to a rotating magnetic field of sufficient strength to cause the caudal rod portion to rotate relative to the cranial rod portion.

The method may involve the use of a bilateral construct, such as that shown in FIG. 1. Such embodiments of the method will comprise fastening at least a second bone anchor to the cervical vertebra, and may comprise fastening additional bone anchors to other vertebrae. Methods of bilateral fixation will also comprise connecting a second jointed spinal rod assembly (which may be any embodiment of the jointed spinal rod described above) to the second bone anchor and the occipital plate. Like the first jointed spinal rod, the second jointed spinal rod is connected to the second bone anchor via the caudal rod portion, and connected to the occipital plate via the cranial rod portion. The relative inclination of the cranial and caudal rod portions of the second jointed rod assembly are also adjusted by exposure to a rotating magnetic field. Although such adjustment may occur at any time, in some embodiments of the method adjustment is performed post-operatively. Post-operative adjustment may be performed while the subject is conscious. In a specific embodiment, post-operative adjustment is performed post-operatively but prior to fusion.

The method may comprise engaging the locking mechanism in the jointed spinal rod after adjusting the relative inclination of the caudal rod portion of the spinal rod assembly to the cranial rod portion of the rod assembly. This may be accomplished by exposing the locking mechanism to a remote signal, such as a rotating magnetic field. Although such locking may occur at any time, in some embodiments of the method locking is performed post-operatively. Post-operative locking may be performed while the subject is conscious. In a specific embodiment, post-operative locking is performed post-operatively but prior to fusion. In further embodiments the locking mechanism may be disengaged post-operatively. For example, the joint might be locked during surgery, unlocked post-operatively to allow adjustment of the rod, and then locked again once proper adjustment has been achieved. Alternatively, the rod may remain unlocked for the duration of surgery, and then only locked after post-operative adjustment has been completed (or after a post-operative evaluation concludes that no adjustment is needed).

Figure 7:
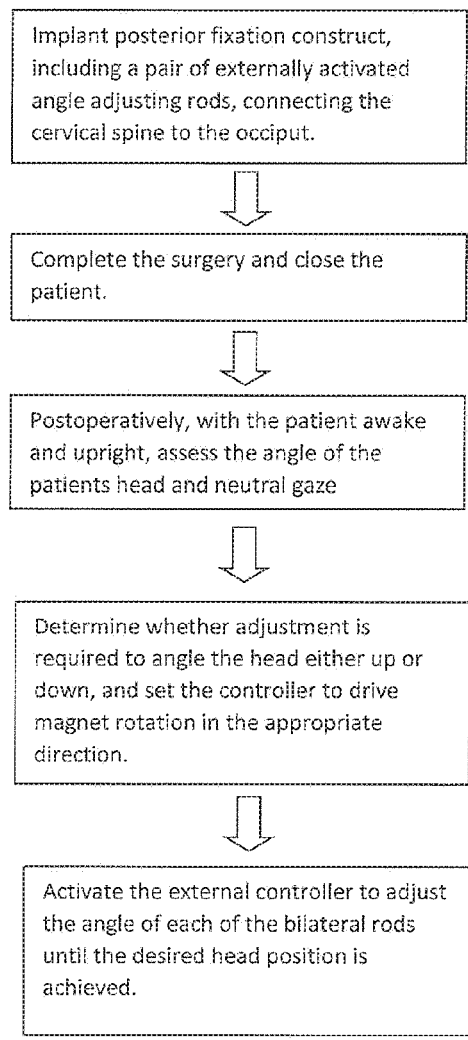
FIG. 7. A flowchart of an exemplary embodiment of the method of fixing the relative positions of a cervical vertebra and an occipital bone in a subject.

The post-operative adjustment of the jointed rod assembly will have the effect of adjusting the inclination of the subject's head relative to the neck or thorax. Among other things, this determines the vertical angle of the subject's gaze, which controls the scope of the subject's gaze. The scope of the subject's gaze in turn affects the subject's ability to sense his or her surroundings. Consequently it is desirable to assess the angle of the subject's head and the subject's neutral gaze (the direction of the patient's gaze when the eyes are pointed directly ahead relative to the head) before adjusting the angle of the jointed spinal rod. If adjustment is necessary for the subject's neutral gaze to be roughly parallel to the ground, then an embodiment of the external controller may be brought into proximity with the jointed rod assembly and the controller's external magnets may be rotated. This creates a rotating magnetic field that causes the jointed rod assembly to change its angulation. Depending on whether the angle of the head needs to be increased or decreased, the external magnet or magnets will be rotated in one direction or another. A flowchart of an exemplary embodiment of the method is shown in FIG. 7.

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 and related laws or otherwise to provide organizational queues. These headings shall not limit or characterize the invention(s) set forth herein.

The following is claimed:

1. A cervical fixation system for fixing the relative positions of a cervical vertebra and an occipital bone in a subject, the system comprising:
   a jointed spinal rod assembly having a longitudinal length sufficient to extend from the vertebra to the occipital bone, and comprising a caudal rod portion, a cranial rod portion, and an adjustment mechanism connectable to the caudal rod portion and the cranial rod portion, and configured to rotate the caudal and cranial rod portions relative to one another about a joint axis that is generally perpendicular to the longitudinal axes of the caudal and cranial rod portions, said rotation occurring in response to a rotating magnetic field; and
   a bone anchor having a bone fastener connected to a rod housing, said rod housing dimensioned to accept the caudal rod portion of the spinal rod assembly; and an occipital plate member having a fixation screw, and a rod receiver dimensioned to accept the cranial rod portion of the spinal rod assembly, wherein the adjustment mechanism comprises a magnetically-activated locking mechanism configured to prevent rotation of the caudal rod portion relative to the cranial rod portion when engaged, but to allow rotation of the caudal rod portion relative to the cranial rod portion when not engaged.

2. The cervical fixation system of claim 1, comprising: a second spinal rod assembly; and a crossbar, said crossbar dimensioned to fit between two spinous processes of two adjacent cervical vertebra, and comprising: a first rod connector at a first end configured to connect the crossbar to the caudal rod portion, and a second rod connector at a second end configured to connect the crossbar to a rod portion of the second spinal rod assembly.

3. The cervical fixation system of claim 2, wherein: the second spinal rod assembly is a second jointed rod assembly, and comprises a second caudal rod portion connected to a second adjustment mechanism, and a second cranial rod portion connected to the second adjustment mechanism, said second spinal rod assembly having a longitudinal length sufficient to extend from the vertebra to the occipital bone; the second adjustment mechanism is configured to rotate the second caudal and second cranial rod portions relative to one another about a second joint axis that is generally perpendicular to the longitudinal axes of the second caudal and second cranial rod portions; the cervical fixation system comprises a second bone anchor dimensioned to accept the second caudal rod portion; and the occipital plate member has a second rod receiver dimensioned to accept the second cranial rod portion.

4. The cervical fixation system of claim 1, wherein the caudal rod portion is seated in the rod housing of the bone anchor, and the cranial rod portion is fastened to the rod receiver of the occipital plate.

5. The cervical fixation system of claim 1, wherein the jointed spinal rod assembly, bone anchor, and occipital plate are at least partially composed of a non-absorbable biocompatible material.

6. The cervical fixation system of claim 1, wherein the jointed spinal rod assembly, bone anchor, and occipital plate are at least partially composed of a non-absorbable biocompatible material selected from the group consisting of: titanium, alloys of titanium, steel, stainless steel, austenitic stainless steel, aluminum oxide, calcium oxide, calcium phosphate, hydroxyapatite, zirconium oxide, and polypropylene.

7. The cervical fixation system of claim 1, wherein the caudal rod portion is connected to the adjustment mechanism.

8. The cervical fixation system of claim 1, wherein the cranial rod portion is connected to the adjustment mechanism.

9. The cervical fixation system of claim 1, wherein the caudal rod portion is connected to the adjustment mechanism and the cranial rod portion is connected to the adjustment mechanism.

10. The cervical fixation system of claim 1, wherein the adjustment mechanism is configured to rotate the caudal and cranial rod portions relative to one another about exactly one joint axis.

11. The cervical fixation system of claim 1, wherein the adjustment mechanism is operatively linked to a first magnet configured to rotate when exposed to a rotating magnetic field; and wherein the adjustment mechanism is configured to rotate the caudal rod portion relative to the cranial rod portion in response to the rotation of the first magnet.

12. The cervical fixation system of claim 11, wherein the adjustment mechanism apart from the first magnet is composed of one or more non-magnetic or weakly magnetic materials.

13. The cervical fixation system of claim 11, wherein the adjustment mechanism apart from the first magnet is composed of one or more non-magnetic or weakly magnetic materials selected from the group consisting of: titanium, aluminum oxide, calcium oxide, calcium phosphate, hydroxyapatite, zirconium oxide, polypropylene, and austenitic stainless steel.

14. The cervical fixation system of claim 11, wherein the first magnet is a quadrupole magnet.

15. The cervical fixation system of claim 11, comprising a gear train to translate the rotation of the first magnet into inclination of the caudal rod portion relative to the cranial rod portion.

16. The cervical fixation system of claim 15, wherein the gear train comprises a rotatable worm that is driven by the first magnet, a worm wheel engaged to be driven by the worm, and a grooved surface on the cranial rod portion having a plurality of grooves engaged to the worm wheel.

17. The cervical fixation system of claim 15, wherein the gear train comprises a rotatable worm that is driven by the first magnet, and a grooved surface on the cranial rod portion having a plurality of grooves engaged to the worm.

18. A cervical fixation system for fixing the relative positions of a cervical vertebra and an occipital bone in a subject, the system comprising: a jointed spinal rod assembly having a longitudinal length sufficient to extend from the vertebra to the occipital bone, and comprising a caudal rod portion, a cranial rod portion, and an adjustment mechanism connectable to the caudal rod portion and the cranial rod portion, and configured to rotate the caudal and cranial rod portions relative to one another about a joint axis that is generally perpendicular to the longitudinal axes of the caudal and cranial rod portions, said rotation occurring in response to a rotating magnetic field; a bone anchor having a bone fastener connected to a rod housing, said rod housing dimensioned to accept the caudal rod portion of the spinal rod assembly; and an occipital plate member having a fixation screw, and a rod receiver dimensioned to accept the cranial rod portion of the spinal rod assembly, wherein the adjustment mechanism is operatively linked to a first magnet configured to rotate when exposed to a rotating magnetic field; and wherein the adjustment mechanism is configured to rotate the caudal rod portion relative to the cranial rod portion in response to the rotation of the first magnet, and wherein the first magnet is mounted to the adjustment mechanism to allow said first magnet to rotate about a longitudinal axis of one of the caudal rod portion and the cranial rod portion.

19. A cervical fixation system for fixing the relative positions of a cervical vertebra and an occipital bone in a subject, the system comprising: a jointed spinal rod assembly having a longitudinal length sufficient to extend from the vertebra to the occipital bone, and comprising a caudal rod portion, a cranial rod portion, and an adjustment mechanism connectable to the caudal rod portion and the cranial rod portion, and configured to rotate the caudal and cranial rod portions relative to one another about a joint axis that is generally perpendicular to the longitudinal axes of the caudal and cranial rod portions, said rotation occurring in response to a rotating magnetic field; a bone anchor having a bone fastener connected to a rod housing, said rod housing dimensioned to accept the caudal rod portion of the spinal rod assembly; and an occipital plate member having a fixation screw, and a rod receiver dimensioned to accept the cranial rod portion of the spinal rod assembly, wherein the adjustment mechanism is operatively linked to a first magnet configured to rotate when exposed to a rotating magnetic field; and wherein the adjustment mechanism is configured to rotate the caudal rod portion relative to the cranial rod portion in response to the rotation of the first magnet, wherein the first magnet directly drives the adjustment mechanism.

* * * * *